United States Patent [19]

Heckele

[11] Patent Number: 5,020,514

[45] Date of Patent: Jun. 4, 1991

[54] ENDOSCOPE FOR NASAL SURGERY

[75] Inventor: Helmut Heckele, Knittlingen, Fed. Rep. of Germany

[73] Assignee: Richard Wolf GmbH, Knittlingen, Fed. Rep. of Germany

[21] Appl. No.: 527,221

[22] Filed: May 22, 1990

[30] Foreign Application Priority Data

Jul. 19, 1989 [DE] Fed. Rep. of Germany ....... 3923851

[51] Int. Cl.⁵ .............................................. A61B 1/00
[52] U.S. Cl. ....................................................... 128/4
[58] Field of Search ......................................... 128/4, 6

[56] References Cited

U.S. PATENT DOCUMENTS

| 4,653,476 | 3/1987 | Bonnet | 128/4 |
| 4,706,655 | 11/1987 | Krauter | 128/4 |
| 4,750,475 | 6/1988 | Yoshihashi | 128/6 |
| 4,756,303 | 7/1988 | Kawashima et al. | 128/6 |
| 4,771,766 | 9/1988 | Aoshiro et al. | 128/4 |
| 4,881,523 | 11/1989 | Heckele | 128/4 |

Primary Examiner—William H. Grieb
Attorney, Agent, or Firm—Panitch, Schwarze, Jacobs & Nadel

[57] ABSTRACT

An endoscope for nasal surgery comprises an outer shaft having a handle incorporating a switching valve for connecting a suction and flushing channel of the outer shaft to, and disconnecting it from, a source of negative pressure and a source of flushing fluid. A working insert for insertion into the outer shaft, comprises a shaft for receiving an optical system proximally connected to the working insert, a shaft having a proximally positioned connector for insertion therethrough of an auxiliary instrument, for example a pair of forceps, and two guides for wires or rods which are movable by means of handles pivoted to the proximal end part of the working insert to displace a lever on the distal end of the working insert angularly to adjust the distal end of the auxiliary instrument.

5 Claims, 2 Drawing Sheets

ENDOSCOPE FOR NASAL SURGERY

FIELD OF THE INVENTION

This invention relates to an endoscope for nasal surgery, that is to say a rhinoscope.

BACKGROUND OF THE INVENTION

There is disclosed in DE-B-38 03 212 (U.S. Pat. No. 4,881,523) an endoscope for nasal surgery having an outer endoscope shaft comprising a suction and flushing shaft and a handle connected to the outer shaft, a switching valve being provided in the handle for connecting the suction and flushing shaft to, and disconnecting it from, a source of negative pressure and a flushing fluid source. An optical system extends centrally through the endoscope shaft, so that a further shaft for receiving a surgical instrument cannot be provided.

SUMMARY OF THE INVENTION

An object of the invention is to provide means enabling an auxiliary instrument, for example a laser probe, a pair of forceps or the like, to be passed through the endoscope for nasal surgery and to be led distally thereof under visual observation to a site of treatment in the bodily cavity concerned, the supply and discharge of flushing fluid also being provided for.

According to the invention, therefore, there is couplable to the outer shaft proximally of the handle, a working insert comprising a shaft for an auxiliary instrument which is to be inserted proximally through an angled connector, a shaft for an optical system arranged to be connected proximally to the working insert and at both sides thereof an angularly displaceable operating handle for wires or rods acting on a lever for pivotally displacing the distal end of the instrument.

Another object of the invention is to provide means whereby an auxiliary instrument for a left-handed, as well as a right-handed, user can readily be passed through the endoscope and manipulated. To this end, the proximal end portion of the instrument receiving shaft is angled with respect to the longitudinal axis of the endoscope and is provided with a bearing allowing angular displacement of the angled connector for the auxiliary instrument to be passed therethrough.

The proximal end portion of the instrument receiving shaft can accordingly be angularly displaced with respect to the axis of that shaft, by appropriately angularly displacing the angled connector in its bearing to the left or to the right of the handle for ready insertion of the auxiliary instrument through the connector by a left-handed, or a right-handed, user as the case may be.

DETAILED DESCRIPTION OF THE INVENTION

Figure 1:
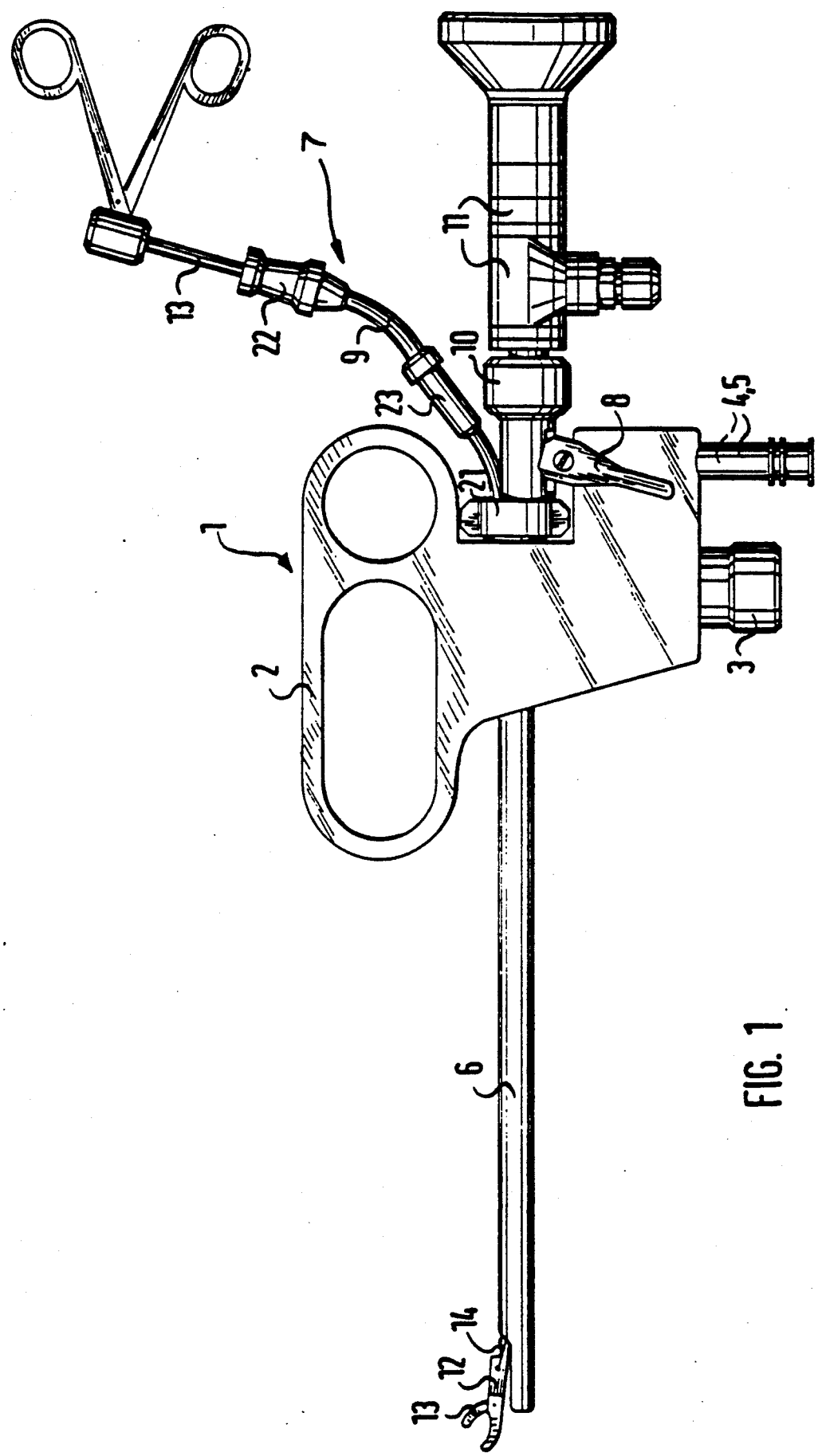
FIG. 1 is a side view of an endoscope for nasal surgery, according to an embodiment of the invention.
Figure 4:
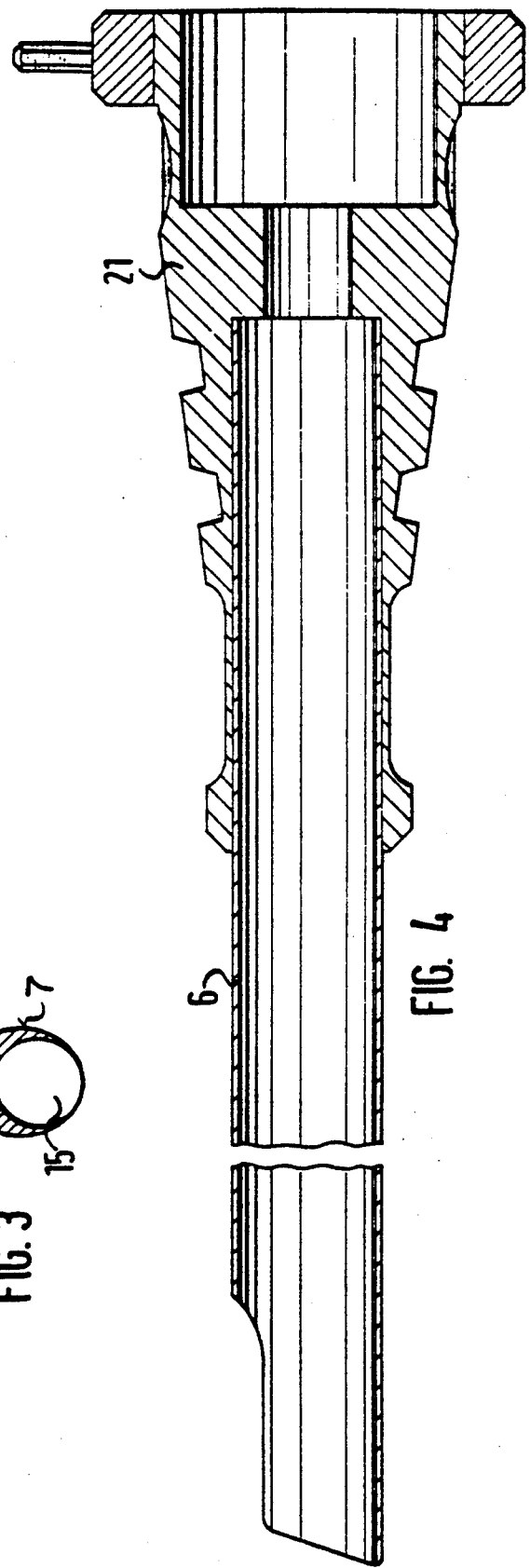
FIG. 4 is an enlarged longitudinally sectional view of said outer shaft.

An endoscope 1 for nasal surgery, which is shown in FIG. 1 comprises an outer endoscope shaft 6 (best seen in FIG. 4) incorporating a flushing and suction shaft. A handle 2 connected to the shaft has therein a switching valve 3 constructed according to the teaching of DE-B-38 03 212 (U.S. Pat. No. 4,881,523) which is hereby incorporated herein by reference, and which has connectors 4 and 5 for coupling to respective sources of negative pressure and flushing fluid. The valve serves to connect the flushing and suction shaft to, and to disconnect it from, said sources according to need. A working insert 7 (best seen in FIG. 2) is releasably connectable to the proximal end of the shaft 6 to extend therethrough. On either side of the handle 2 the insert 7 has pivotally attached thereto an operating handle 8. An angled connector 9, for the insertion therethrough of an auxiliary instrument 13, in the present example a pair of forceps for use at a site of treatment in the nose cavity, is connected for angular displacement about its longitudinal axis, near the proximal end of the insert 7. The insert 7 has, communicating with the connector 9, a shaft 16 for receiving the instrument 13, the connector 9 being proximal of the handle 2 when the insert 7 has been assembled to the shaft 6 as shown in FIG. 1. The insert 7 has pivotally connected to its distal end an "Albarran" or like lever 12 for pivotal deflection of the distal end of the instrument 13, through a limited angle with respect to the longitudinal axis of the endoscope 1. An optical system 11 is attachable to the proximal end of the insert 7 by means of a coupling 10.

Figure 2:
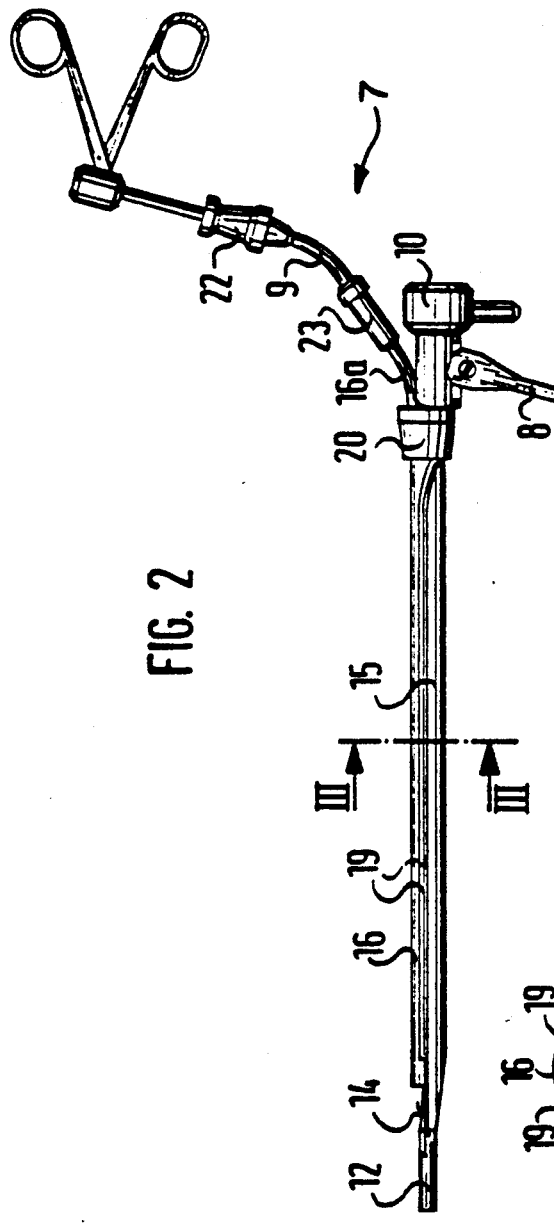
FIG. 2 is a side view of a working insert of the endoscope.

The insert 7 comprises a further shaft 15, through which the optical system 11 extends and which has an open distal end portion which is inclined upwardly as shown in FIG. 2 with respect to the axis of the shaft 16, and to which the lever 12 is pivotally attached. The lever 12 is coupled by means of one or more traction and thrust rods or wires 14 to the handles 8 and to an axially displaceable rod (not shown) in engagement therewith whereby the lever 12 and thus said distal end of the instrument 13 are displaceable at an angle with respect to the longitudinal axis of the instrument 13, by pivotal adjustment of at least one of the handles 8, when the instrument 13 has been inserted through the connector 9.

Figure 3:
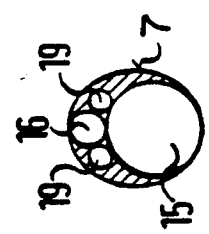
FIG. 3 is a cross-sectional view taken on the lines III—III of FIG. 2.

The rods or wires 14 which run along either side of the shaft 16 for the instrument 13, extend through guides 19, best seen in FIG. 3, fixed to the upper side of the shaft 15 of the insert 7. The endoscope shaft 6 and the insert 7 which is insertable therethrough, and releasably connected by means of a tapered end coupling 20 and a clamping ring 21. The insert 7 and the shaft 6 could, however, be non-releasably connected together so as to form an integral unit.

The shaft 16 is angled at 16a away from the axis of the shaft 15, proximally of the coupling 20 and is secured to the connector 9 by means of a bearing 23 in which the connector 9, which is provided with a hose connector 22, is rotatable about its axis, so that it can be pivotally displaced both rightwardly and leftwardly of the handle 2, for adaption to either a right-handed or to a left-handed user, thereby to facilitate the user in inserting and operating the instrument 13. A handle 8 is provided on either side of the insert 7, in order to facilitate operation of the lever 12 either by a right-handed or by a left-handed user.

WHAT IS CLAIMED IS

1. An endoscope for nasal surgery, comprising:
   an outer endoscope shaft incorporating a suction and flushing shaft;

a handle connected to the outer shaft, in which handle is provided a switching valve for connecting the suction and flushing shaft to, and disconnecting it from, a negative pressure source and a flushing fluid source;

a working insert for the outer shaft couplable thereto proximally of the handle and having a shaft for receiving an auxiliary instrument inserted thereinto by way of an angled connector on said insert, and a shaft for receiving an optical system connectable proximally to said insert;

a lever on said insert for pivotally displacing a distal end of the auxiliary instrument when said instrument is received in said instrument receiving shaft;

an angularly displaceable operating handle for said lever, on either side of said insert; and elongate means connecting said handles to said lever for angular displacement thereof by angular displacement of said handles.

2. An endoscope as claimed in claim 1, wherein said elongate means comprises at least one wire.

3. An endoscope as claimed in claim 1, wherein said elongate means comprises at least one rod.

4. An endoscope as claimed in claim 1, wherein said angled connector is angled with respect to a longitudinal axis of said endoscope, and is provided with a bearing for angular displacement of the angled connector.

5. An endoscope as claimed in claim 4, wherein said elongate means run through guides, said guides and said instrument receiving shaft being fixedly connected to said optical system receiving shaft as a single unit.

* * * * *